US009795704B2

(12) United States Patent
Pugh et al.

(10) Patent No.: US 9,795,704 B2
(45) Date of Patent: Oct. 24, 2017

(54) OPHTHALMIC LENS DISINFECTING BASE

(71) Applicant: Johnson & Johnson Vision Care, Inc., Jacksonville, FL (US)

(72) Inventors: Randall B Pugh, Jacksonville, FL (US); Edward R Kernick, Jacksonville, FL (US); William Chester Neeley, Melbourne, FL (US); Dwight Abouhalkah, Jacksonville, FL (US); Leslie A Voss, Jacksonville, FL (US); Karson S Putt, Jacksonville, FL (US); James Daniel Riall, St. Johns, FL (US)

(73) Assignee: Johnson & Johnson Vision Care, Inc, Jacksonville, FL (US)

( * ) Notice: Subject to any disclaimer, the term of this patent is extended or adjusted under 35 U.S.C. 154(b) by 0 days.

(21) Appl. No.: 15/066,071

(22) Filed: Mar. 10, 2016

(65) Prior Publication Data
US 2016/0184472 A1 Jun. 30, 2016

Related U.S. Application Data

(63) Continuation of application No. 12/961,616, filed on Dec. 7, 2010, now abandoned.

(60) Provisional application No. 61/346,162, filed on May 19, 2010.

(51) Int. Cl.
*A61L 12/06* (2006.01)
*A45C 11/00* (2006.01)

(52) U.S. Cl.
CPC ......... *A61L 12/063* (2013.01); *A45C 11/005* (2013.01)

(58) Field of Classification Search
USPC .................................................. 250/455.11
See application file for complete search history.

(56) References Cited

U.S. PATENT DOCUMENTS

| 3,621,855 | A | | 11/1971 | Rabinowitz |
| 3,852,032 | A | | 12/1974 | Urbach |
| 3,978,341 | A | | 8/1976 | Hoell |
| 4,063,890 | A | | 12/1977 | Baron |
| 4,412,834 | A | | 11/1983 | Kulin |
| 4,529,868 | A | | 7/1985 | Bowen |
| 4,545,479 | A | * | 10/1985 | Figari .................. A45C 11/005 132/286 |

(Continued)

FOREIGN PATENT DOCUMENTS

CN 101401949 4/2009
DE 29509210 10/1995

(Continued)

OTHER PUBLICATIONS

William A. Rutala, David J. Weber, and the Healthcare Infection Control Practices Advisory Committee, "Guideline for Disinfection and Sterilization in Healthcare Facilities", Center for Disease Control, 2008.

(Continued)

*Primary Examiner* — Phillip A Johnston

(57) ABSTRACT

The present invention provides for a disinfecting radiation base for working in conjunction with a storage case for an ophthalmic lens. The disinfecting radiation base provides disinfecting radiation for disinfecting an ophthalmic lens. The disinfecting radiation base may also include a processor and digital memory for automated functions associated with the base.

23 Claims, 5 Drawing Sheets

(56) References Cited

U.S. PATENT DOCUMENTS

| | | | |
|---|---|---|---|
| 4,735,223 A * | 4/1988 | Ituarte | A61L 12/026 134/184 |
| 4,868,397 A | 9/1989 | Tittel | |
| 5,120,499 A * | 6/1992 | Baron | A61L 12/026 250/455.11 |
| 5,144,144 A | 9/1992 | Borovsky | |
| 5,439,642 A | 8/1995 | Hagmann | |
| 5,440,458 A | 8/1995 | Volk | |
| 5,618,492 A | 4/1997 | Auten | |
| 6,030,554 A | 2/2000 | Ichihara | |
| 6,461,568 B1 | 10/2002 | Eckhardt | |
| 6,592,816 B1 * | 7/2003 | Ebel | A61L 2/10 250/455.11 |
| 6,790,409 B1 | 9/2004 | Nakamura | |
| 7,169,037 B2 | 1/2007 | Lin | |
| 7,217,936 B2 | 5/2007 | Ressler | |
| 7,879,288 B2 | 2/2011 | Brown-Skrobot | |
| 8,277,741 B2 * | 10/2012 | McCabe | A61L 2/10 422/105 |
| 8,528,728 B2 * | 9/2013 | Pugh | A45C 11/005 206/5.1 |
| 8,969,830 B2 | 3/2015 | Pugh | |
| 9,282,796 B2 | 3/2016 | Pugh | |
| 2004/0210123 A1 | 10/2004 | Davidson | |
| 2004/0234569 A1 | 11/2004 | Nakada | |
| 2005/0013729 A1 | 1/2005 | Brown-Skrobot | |
| 2005/0028848 A1 | 2/2005 | Lai | |
| 2005/0079096 A1 | 4/2005 | Brown-Skrobot | |
| 2005/0173652 A1 | 8/2005 | Ressler | |
| 2007/0104611 A1 | 5/2007 | Marmo | |
| 2007/0206377 A1 * | 9/2007 | Borup | A45C 11/005 362/156 |
| 2008/0260601 A1 | 10/2008 | Lyon | |
| 2009/0086160 A1 | 4/2009 | Enns | |
| 2009/0096351 A1 | 4/2009 | Hampden-Smith | |
| 2009/0256085 A1 | 10/2009 | Thiruppathi | |
| 2009/0274576 A1 | 11/2009 | Ressler | |
| 2010/0266445 A1 | 10/2010 | Campagna | |
| 2010/0279124 A1 | 11/2010 | Scherer | |
| 2010/0320405 A1 | 12/2010 | Gardner, III | |
| 2011/0284773 A1 | 11/2011 | Pugh | |
| 2012/0138819 A1 | 6/2012 | Pugh | |

FOREIGN PATENT DOCUMENTS

| | | |
|---|---|---|
| EP | 1038536 | 9/2000 |
| EP | 2067491 | 6/2009 |
| FR | 2599255 | 12/1987 |
| GB | 1453372 | 10/1976 |
| JP | 5628763 | 3/1981 |
| JP | 394758 | 4/1991 |
| JP | 3131738 | 6/1991 |
| JP | 4263213 | 9/1992 |
| JP | 7505724 | 9/1992 |
| JP | 7505724 | 2/1993 |
| JP | 7504758 | 5/1995 |
| JP | 3100828 | 6/1995 |
| JP | 7265394 | 10/1995 |
| JP | 866678 | 3/1996 |
| JP | 2000507140 | 10/1997 |
| JP | 10094586 | 4/1998 |
| JP | 63262155 | 10/1998 |
| JP | 2000245815 | 9/2000 |
| JP | 2001066422 | 3/2001 |
| JP | 2001188207 | 7/2001 |
| JP | 2003524558 | 11/2001 |
| JP | 2013532305 | 11/2001 |
| JP | 2002126050 | 5/2002 |
| JP | 2002220211 | 8/2002 |
| JP | 2003093481 | 4/2003 |
| JP | 2004159676 | 6/2004 |
| JP | 2004275335 | 10/2004 |
| JP | 2007522843 | 8/2005 |
| JP | 2008510538 | 3/2006 |
| JP | 2007152121 | 6/2007 |
| JP | 2010540113 | 4/2009 |
| JP | 2013530422 | 11/2011 |
| KR | 20010092892 | 10/2001 |
| KR | 2003095377 | 12/2003 |
| KR | 20040071084 | 8/2004 |
| KR | 100586927 | 6/2006 |
| KR | 20070050328 | 5/2007 |
| RU | 57423 | 10/2006 |
| RU | 69323 | 10/2007 |
| TW | 202793 | 3/1981 |
| TW | M256699 | 2/2005 |
| TW | M329760 | 10/2007 |
| TW | M367032 | 10/2009 |
| WO | WO 9805438 | 2/1998 |
| WO | WO 9938540 | 8/1999 |
| WO | WO 2005/077076 | 8/2005 |
| WO | WO 2006105180 | 10/2006 |
| WO | WO 2007046226 | 4/2007 |
| WO | WO 2011146497 | 11/2011 |
| WO | WO 2011146505 | 11/2011 |

OTHER PUBLICATIONS

Harris, M.G., et al. "Ultraviolet Disinfection of Contact Lenses." Optometry and Vision Science, Oct. 1993;70(10): 839-42.

Admoni, M.M., et al. "Disinfection Efficacy in an Integrated Ultraviolet Light Contact Lens Care System." CLAO J. Oct. 1994; 20(4): 246-8.

Dolman, P.J., et al. "Contact Lens Disinfection by Ultraviolet Light." American Journal of Ophthalmology, Dec. 15, 1989;108(6):665-9.

"UV Kills These Bugs", Review of Optometry. Dec. 15, 1999 vol. 136 i12 p. 62.

"Device Cleans, Disinfects Soft Contact Lenses in 15 Minutes." Ophthalmology Times., Apr. 15, 2004 vol. 29 i8 p. 66.

PCT International Search Report, dated May 7, 2013, for PCT Int'l Appln. No. PCT/US2013/023010.

International Search Report for corresponding Application No. PCT/US2011/036836 dated Aug. 3, 2011.

International Search Report for corresponding Application No. PCT/US2011/036832 dated Aug. 3, 2011.

International Search Report for corresponding Application No. PCT/US2011/036826 dated Aug. 3, 2011.

* cited by examiner

OPHTHALMIC LENS DISINFECTING BASE

REFERENCE TO RELATED APPLICATIONS

Cross Reference to Related Applications

This application continuation of U.S. patent application Ser. No. 12/961,616, filed Dec. 7, 2010, entitled "OPHTHALMIC LENS DISINFECTING BASE" which is a non-provisional filing claiming priority to provisional application, U.S. Ser. No. 61/346,162, filed on May 19, 2010 and entitled "OPHTHALMIC LENS DISINFECTING BASE," the contents of which are relied upon and incorporated by reference.

FIELD OF USE

This invention describes a case for storing an ophthalmic lens and, more specifically, in some embodiments, a base for receiving a case with disinfecting functionality while storing an ophthalmic lens such as a contact lens.

BACKGROUND

It is well known that contact lenses can be used to improve vision. Various contact lenses have been commercially produced for many years. Early designs of contact lenses were fashioned from hard materials. Although these lenses are still currently used in some applications, they are not suitable for all patients due to their poor comfort and relatively low permeability to oxygen. Later developments in the field gave rise to soft contact lenses, based upon hydrogels.

Hydrogel contact lenses are very popular today. These lenses are often more comfortable to wear than contact lenses made of hard materials. Many hydrogel contact lenses may be worn for more than one day. However, a build-up of microbial life and bacteria on the lenses generally makes it desirable to periodically remove the lenses and disinfect them.

Disinfection of contact lenses traditionally entails placing the contact lens in a container or case and subjecting the contact lens to a chemical disinfectant. However, chemical disinfectants are not always as efficacious as may be desired. From time to time, a contact lens with a bacterium, mold, fungus or other type of adverse life form is reinserted into a user's eye with the result being a diseased eye. In addition, disinfecting solutions tend to be expensive and add to the total cost of using contact lenses for vision correction or cosmetic enhancement. New methods and approaches are therefore needed to disinfect contact lenses.

SUMMARY

Accordingly, the present invention includes a base for an ophthalmic lens storage case for storing reusable contact lenses and disinfecting the lenses during the storage. The lens storage case is capable of receiving disinfecting radiation in a wavelength and intensity suitable to kill unwanted bacteria, viruses, molds, fungi and the like on a contact lens. The base is capable of providing disinfecting radiation in a wavelength and intensity suitable to kill the unwanted bacteria, viruses, molds, fungi and the like on a contact lens.

In addition, in some embodiments, the base provides vibrational frequency mechanically sufficient to effectively dislocate expired microbials and provide increased exposure of unexpired microbials to life extinguishing radiation.

In another aspect, in some embodiments, a disinfecting radiation base includes one or more reflective surfaces, such as a mirror, for reflecting disinfecting radiation towards an ophthalmic lens stored in a storage case mounted in the disinfecting radiation base.

DETAILED DESCRIPTION OF THE INVENTION

The present invention includes methods and apparatus for disinfecting an ophthalmic lens. In addition, the present invention includes a storage case for holding an ophthalmic lens while it is disinfected with disinfecting radiation.

In the following sections detailed descriptions of embodiments of the invention will be given. The description of both preferred and alternative embodiments are exemplary embodiments only, and it is understood that to those skilled in the art that variations, modifications and alterations may be apparent. It is therefore to be understood that said exemplary embodiments do not limit the scope of the underlying invention.

GLOSSARY

In this description and claims directed to the presented invention, various terms may be used for which the following definitions will apply:

Disinfecting Radiation: as used herein refers to a frequency and intensity of radiation sufficient to diminish the life expectancy of a life form receiving a Disinfecting Radiation Dose.

Disinfecting Radiation Dose: as used herein refers to an amount of radiation to reduce an amount of life by at least two logs on a logarithmic scale and preferably three logs or more, wherein life includes at least bacteria, viruses, molds and fungi.

Lens: refers to any ophthalmic device that resides in or on the eye. These devices can provide optical correction or may be cosmetic. For example, the term lens can refer to a contact lens, intraocular lens, overlay lens, ocular insert, optical insert or other similar device through which vision is corrected or modified, or through which eye physiology is cosmetically enhanced (e.g. iris color) without impeding vision. In some embodiments, the preferred lenses of the invention are soft contact lenses made from silicone elastomers or hydrogels, which include but are not limited to silicone hydrogels, and fluorohydrogels.

Figure 1:
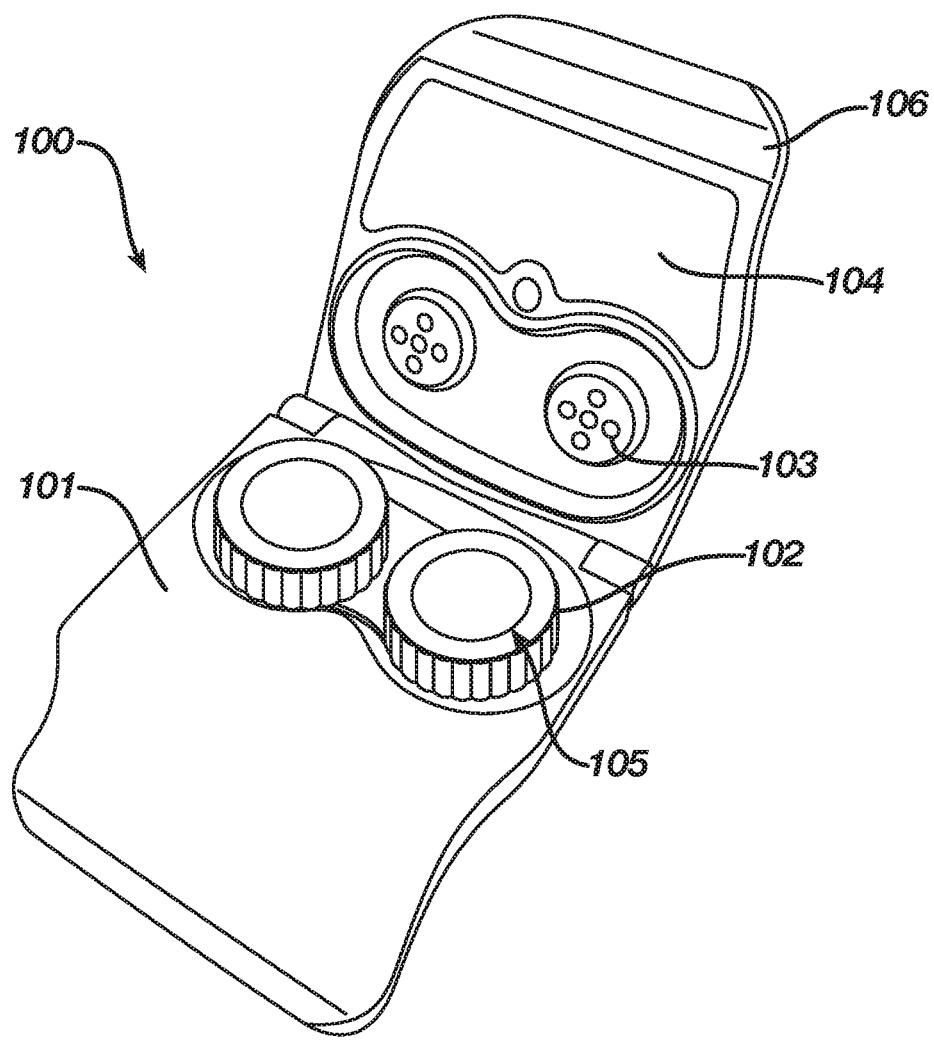
FIG. 1 illustrates a lens storage case in a base unit according to some embodiments of the present invention.

Referring now to FIG. 1, an ophthalmic lens disinfecting system 100 is illustrated including a radiation disinfecting base 101, a radiation disinfecting storage case 102 and a disinfecting radiation source 103. According to the present invention, a radiation disinfecting storage case 102 is positioned within the path of radiation from the radiation disinfecting source 103, such that one or more ophthalmic lenses stored within the radiation disinfecting storage case 102 are exposed to radiation emanating from the radiation disinfecting source 103 and life forms existing on, or in proximity to, the ophthalmic lenses are exposed to the disinfecting radiation, provided by a radiation disinfecting source, and killed, essentially disinfecting the ophthalmic lens.

As illustrated, the radiation disinfecting storage case 102 is positioned in an open state with a radiation disinfecting base 101 and a lid 106. In some preferred embodiments, the radiation disinfecting storage case 102 includes a positioning artifact 105 for aligning the disinfecting radiation source 103 with the radiation disinfecting storage case 102. As illustrated, the positioning artifact 105 includes an annular depression for receiving an annular arrangement of disinfecting radiation source 103. Positioning artifacts 105 may include almost any polygon shaped depression. Other embodiments may include one or more alignment pins. In still other embodiments, a positioning artifact 105 may include a snap, a threaded joining or other removably fixed type of joining.

In some embodiments, the positioning artifact 105 aligns the radiation disinfecting radiation source 103 in a position generally orthogonal to an apex of a contact lens stored within the radiation disinfecting storage case 102. In additional embodiments, a positioning artifact 105 aligns the radiation disinfecting radiation source 103 in a position generally orthogonal to a plane extending across a bottom perimeter of a contact lens.

In another aspect, in some embodiments, the positioning artifact may also be capable of transmitting a vibrational frequency from a radiation disinfecting base 101 to the radiation disinfecting storage case 102 and ultimately to a lens stored within the radiation disinfecting storage case 102. The vibrational frequency may be a frequency capable of causing expired life forms to be moved from within a path of radiation to an unexpired life form. Moving the expired life forms allows for more efficacious disinfecting by exposing more unexpired life forms to a direct path of radiation.

The radiation disinfecting radiation source 103 may include one or more light emitting diodes (LEDs). In some preferred embodiments, the LEDs include ultraviolet (UV) emitting LEDs. Preferred embodiments include LEDs which emit light radiation with a wavelength of between about 250 nanometers of light radiation and about 280 nanometers of light radiation, preferably, the wavelength is between 250 nanometers and 275 nanometers, and most preferably 254 nanometers.

Figure 2:
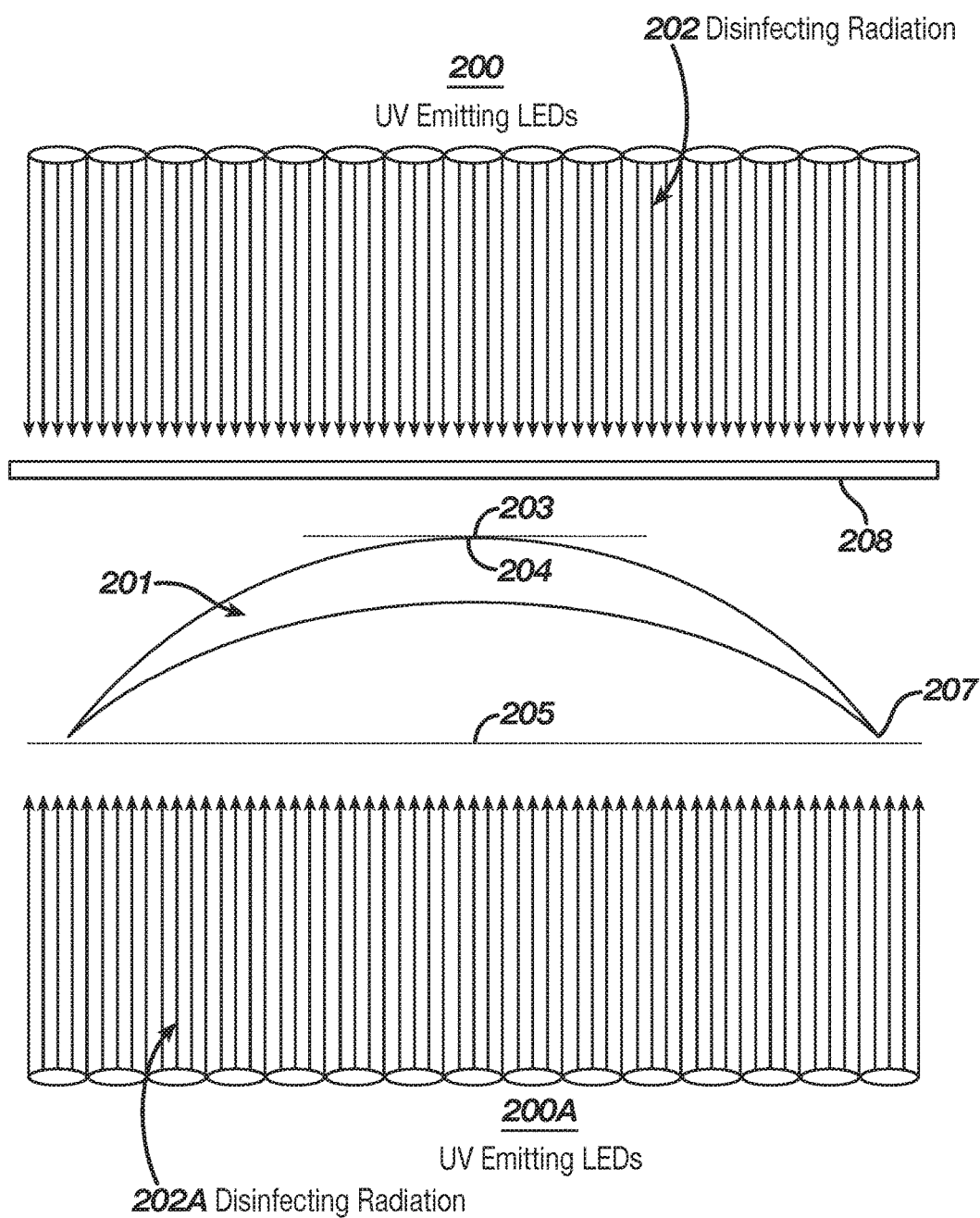
FIG. 2 illustrates some embodiments of alignment of a disinfecting radiation source with an ophthalmic lens in a lens storage case according to the present invention.

Referring now to FIG. 2, a block diagram illustrates some embodiments of alignment of a radiation disinfecting source 200, such as one or more UV LEDs radiating disinfecting radiation 202 in the UV spectrum towards a contact lens 201. In some preferred embodiments, UV LEDs will be arranged such that a radiation disinfecting storage case will align in a specific position in relation to the contact lens 201. The alignment is maintained via an alignment artifact. In some embodiments, a radiation disinfecting storage case is aligned to direct UV radiation 202 at an angle essentially orthogonal to a plane 203 touching an apex 204 of the contact lens 201 retained in a radiation disinfecting storage case.

In other embodiments, radiation disinfecting storage case may be aligned to direct disinfecting radiation 202A from one or more UV emitting LEDs 200A at an angle essentially orthogonal to a plane 205 across a perimeter edge 207 of the contact lens 201.

In another aspect, in some embodiments, one or more optics 208 may be used to focus disinfecting radiation onto a lens stored in a disinfecting radiation storage case. An optic may be included in a base or in a part of a storage case.

Figure 3:
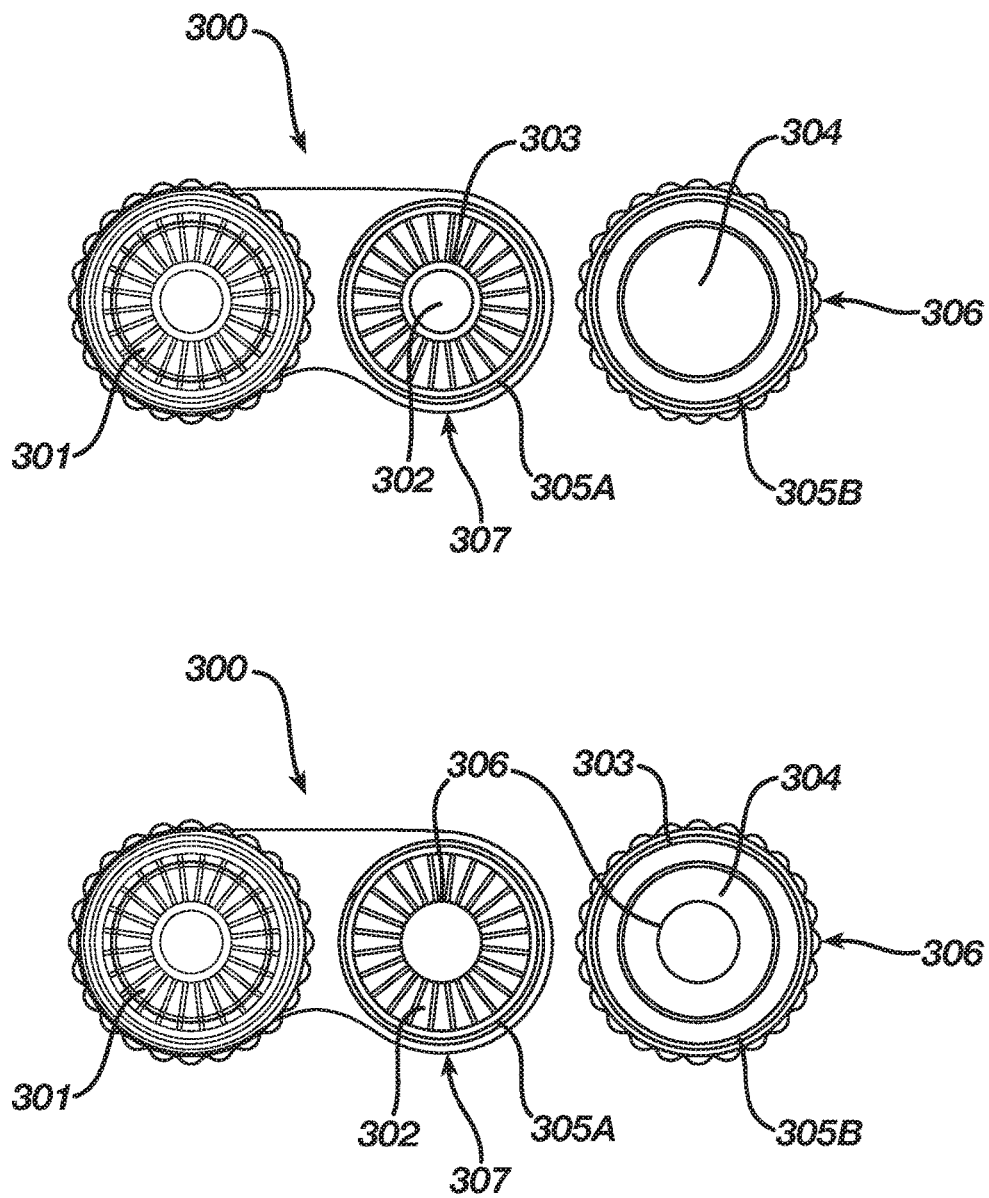
FIG. 3 illustrates a close up view of a storage case with one cap removed according to some embodiments of the present invention.

Referring now to FIG. 3, an exemplary a radiation disinfecting storage case 300 is illustrated. The radiation disinfecting storage case 300 includes one or more lens storage compartments 301. A storage compartment 301 is capable of receiving and storing one or more ophthalmic lenses, such as a contact lens.

Some embodiments include one or more lens alignment mechanisms 302 for positioning an ophthalmic lens stored in a storage compartment 301 included in a radiation disinfecting storage case 300. A lens alignment mechanism 302 may include for example a pedestal with an arcuate surface generally of a similar size and shape as an inside dimension of an ophthalmic lens. A convex surface may include an arc generally equivalent to an arc of a concave surface of an ophthalmic lens to be stored within the radiation disinfecting storage case 300. Other embodiments may include a lens alignment mechanism 306 comprising a bowl generally of a similar size and shape as an outside dimension of an ophthalmic lens.

Preferred positioning aligns the stored lens in a direct path of disinfecting radiation. However, other embodiments may include one or reflective surfaces 306. A reflective surface 306 may essentially include a mirror and be formed from a glass, a plastic, a metal or a coating that is functional to reflect disinfecting radiation in a direction desired. Generally, the direction will be towards a lens stored in a storage case 300 positioned in the base. In some embodiments, reflective surface 306 may be generally proximate to, and/or generally parallel to, a surface of a stored lens. Other embodiments may include a reflective surface 306 generally around a perimeter of a stored lens.

One or more radiation windows 303-304 are included in the storage compartments 301. The radiation windows 303-304 provide portions of the radiation disinfecting storage case that are at least partially transparent to wavelengths of disinfecting radiation. Preferably the radiation windows 303-304 will be as close to 100% transparent as possible to disinfecting radiation transmitted into the storage compartment 301. Plastics that are injection moldable may be 90% or more or even 98% or more transparent to UV radiation. Specific wavelengths may include between about 254 nanometers to 280 nanometers.

In some embodiments, a radiation window may also include an optic for directing disinfecting radiation towards areas of an ophthalmic lens stored in the stored compartment 301.

Examples of materials from which the radiation windows 303-304 may be formed include, for example: cyclic olefins, TOPAS, ZEONOR or other injection moldable plastic. Other plastics or glass may also be utilized as a material for the radiation window 303-304. The area of the radiation windows 303-304 should be sufficient to admit enough disinfecting radition into the storage compartments to kill life forms present on an ophthalmic lens stored in the storage compartment 301.

Some preferred methods of manufacture of a radiation disinfecting storage case include injection molding processes. Other methods include, for example, lathing, stereo lithography, and three dimensional printing.

In another aspect, radiation disinfecting storage case 300 may include a fastening mechanism 305A-305B for securing and removing a cap 306 from a storage compartment 307.

The fastening mechanism 305A-305B may include a threaded portion, a snap, and a tapered joint of other mechanism for removably securing the cap 308 to the case at the discretion of the user. While the cap 308 is secured to the storage compartment 307, the cap seals off an ambient atmosphere from the storage compartment 307 and also contains an ophthalmic lens and, in some embodiments, a solution, such as, for example a saline solution, within the compartment 307.

Figure 4:
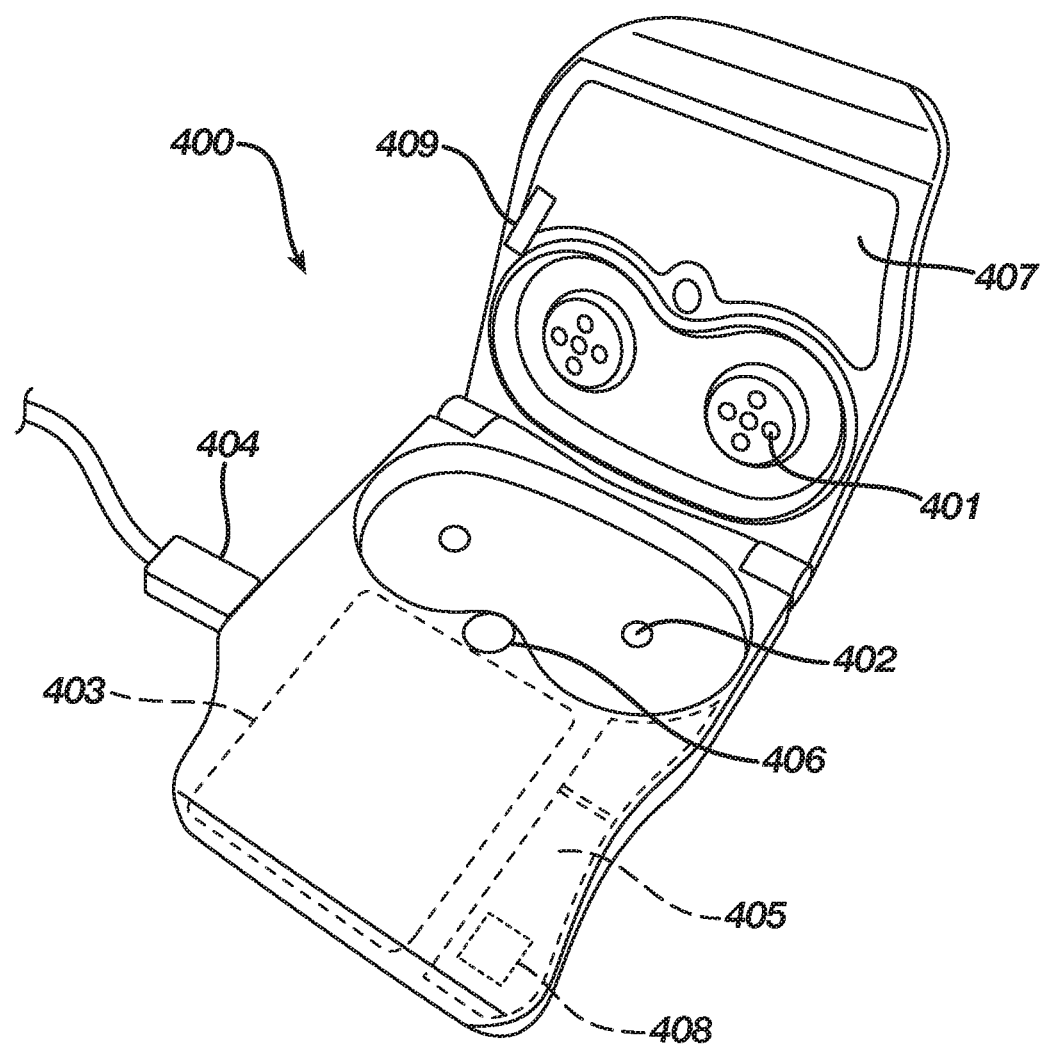
FIG. 4 illustrates aspects of a base unit according to some embodiments of the present invention.

Referring now to FIG. 4, a radiation disinfecting base unit 400 is illustrated with multiple disinfecting radiation source LEDs 401-402. As illustrated, the disinfecting radiation source LEDs 401-402 may include one or both of overhead disinfecting radiation source LEDs 401 and lower disinfecting radiation source LEDs 402. In addition to the overhead disinfecting radiation source LEDs 401 and lower disinfecting radiation source LEDs 402, the base unit may include a processor board 403 with control electronics for controlling various aspects associated with the radiation disinfecting base 400.

The processor board 403 may be coupled to a digital storage 408. The digital storage may include executable software that is executable upon command or automatically upon operation of the radiation disinfecting base unit 400. The digital storage 408 may also store data related to operation of the radiation disinfecting case 400. Operational data may include for example, time periods during which a radiation disinfecting base unit 400 is operated; serial numbers of lenses being disinfected; a period of time that a lens has been placed in use, or other information. In some embodiments, a radiation disinfecting base unit 400 may include a scanner 409 or other input means to input an identification number associated with a lens stored in a radiation disinfecting base unit 400. For example, the scanner 409 may scan a bar code or other symbol on a lens package and log disinfecting information associated with the bar code number or symbol. Information that may be logged may include for example, a number of hours that a lens has been exposed to disinfecting radiation and a number of days that a lens has been placed into use.

An electrical communication connector 404 may also be included in the radiation disinfecting base unit 400. The electrical communication connector 404 may include a universal serial bus (USB) connector or other type of connector. The connector may include a terminal for transferring one or both of data and electrical power. In some embodiments, the electrical communication connector 404 provides power to operate the radiation disinfecting base unit 400. Some embodiments may also include one or more batteries 405 or other power storage device. In some preferred embodiments, the batteries 405 include one or more lithium ion batteries or other rechargeable device. The power storage devices may receive a charging electrical current via the electrical communication connector 404. Preferably, the radiation disinfecting base unit 400 is operational via stored power in the batteries 405.

In some embodiments, the electrical communication connector 404 may include a simple source of AC or DC current.

In another aspect, the present invention may include a source of mechanical movement, such as a vibration generation device 406. The vibration generation device 406 may include, for example, a piezoelectric transducer. A piezoelectric transducer offers a low power reliable device to provide mechanical or vibrational movement.

In some embodiments, the vibrational movement will be adjusted to a frequency that effectively moves dead organisms stored within a storage case in the radiation disinfecting base unit 400. Movement of the dead organisms exposes live organisms that may have otherwise been sheltered from disinfecting radiation.

In still another aspect, in some embodiments, the processor board 403 or other electronic circuitry may control a pattern of light or radiation emitted by the disinfecting radiation source LEDs 401-402. The pattern may include, for example, strobes of a set frequency or variable frequencies.

Some embodiments may also include a display 407. The display 407 will be in logical communication with the processor board 403 and be used to communicate, in human readable form, data relating to the operation of the radiation disinfecting base unit 400.

Figure 5:
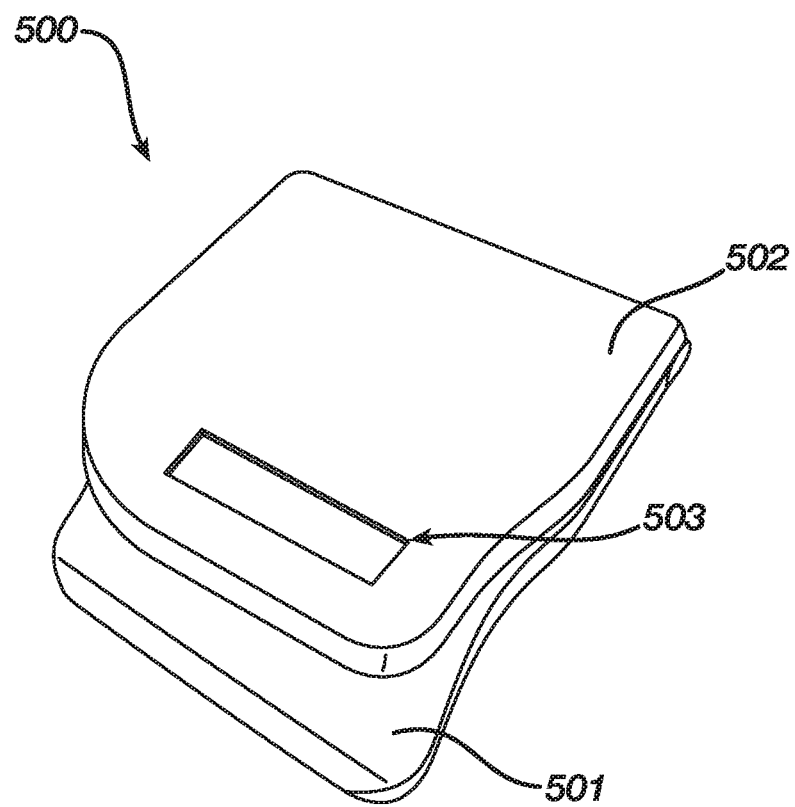
FIG. 5 illustrates a base unit in a closed state with a display.

Referring now to FIG. 5, a radiation disinfecting base unit 500 is illustrated in a closed position. A radiation disinfecting base 501 is covered by a lid 502, in the illustrated embodiments; the lid 502 is hinged to the radiation disinfecting base 501 and folds over on top of the radiation disinfecting base 501. Other embodiments are also within the scope of the invention. As illustrated, a display 503 is located in the lid 502 and may provide an indication of a disinfecting cycle or procedure being executed by the radiation disinfecting base unit 500.

CONCLUSION

The present invention, as described above and as further defined by the claims below, provides apparatus for disinfecting an ophthalmic lens.

The invention claimed is:

1. A base for receiving an ophthalmic lens storage case for storing one or more ophthalmic lenses, the base comprising:
   a receptacle for receiving an ophthalmic lens storage case, wherein said storage case is removable from said receptacle and said storage container includes a removable cap attached to said storage case by a fastening mechanism, wherein said removable cap seals off an ambient atmosphere from a storage compartment with the case and wherein said storage case further comprises an alignment artifact;
   an electronic circuit mounted on said base, wherein said electronic circuit is capable of controlling a predetermined cycle time of radiation exposure;
   a source of disinfecting radiation providing disinfecting radiation to an ophthalmic lens storage compartment in the ophthalmic lens storage case, wherein the disinfecting radiation is capable of permeating the ophthalmic lens storage case and disinfecting an ophthalmic lens stored therein, and wherein said source is controlled by the electronic circuit; and wherein said cap includes a radiation window for directing and focusing disinfecting radiation towards an ophthalmic lens stored in the storage case.

2. The base of claim 1 additionally comprising a reflective surface for reflecting disinfecting radiation towards ophthalmic lens storage compartment.

3. The base of claim 1 additionally comprising a complementary alignment artifact for aligning the source of disinfecting radiation with the ophthalmic lens storage compartment, wherein the complementary alignment artifact is capable of fitting with the alignment artifact included on the storage case.

4. The base of claim 3 wherein the complementary alignment mechanism comprises an alignment post.

5. The base of claim 1 further comprises one or more sources of disinfecting radiation.

6. The base of claim 5 wherein the one or more sources of disinfecting radiation comprise an ultraviolet emitting diode.

7. The base of claim 6 wherein the ultraviolet emitting diode emit radiation in a frequency of between 250 nanometers and 280 nanometers.

8. The base of claim 1 wherein the emitted disinfecting radiation is sufficient kill an organism on an ophthalmic lens stored in the storage compartment.

9. A base for receiving an ophthalmic lens storage case for storing one or more ophthalmic lenses, the base comprising:
a receptacle for receiving an ophthalmic lens storage case, wherein said storage case is removable from said receptacle and said storage container includes a removable cap attached to said storage case by a fastening mechanism, wherein said removable cap seals off an ambient atmosphere from a storage compartment with the case and wherein said storage case further comprises an alignment artifact;
an electronic circuit mounted on said base, wherein said electronic circuit is capable of controlling a predetermined cycle time of radiation exposure; and
a source of disinfecting radiation providing disinfecting radiation to an ophthalmic lens storage compartment in the ophthalmic lens storage case, wherein the disinfecting radiation is capable of permeating the ophthalmic lens storage case and disinfecting an ophthalmic lens stored therein, and wherein said source is controlled by the electronic circuit; and
wherein said cap includes a radiation window for directing and focusing disinfecting radiation towards an ophthalmic lens stored in the storage case, wherein the electronic circuit additionally comprises a processor for controlling the generation of disinfecting radiation.

10. The base of claim 9 wherein a time period that a disinfecting radiation is provided is based upon a logical control signal generated by the processor.

11. The base of claim 9 wherein an intensity at which a disinfecting radiation is provided is based upon a logical control signal generated by the processor.

12. The base of claim 9 additionally comprising an audio component operative to provide an audio signal based upon operation of the source of disinfecting radiation.

13. The base of claim 9 additionally comprising a display for displaying a status of a disinfecting process based upon digital data transmitted by the processor.

14. The base of claim 9 additionally comprising a digital storage for storing information related to a disinfecting process.

15. A base for receiving an ophthalmic lens storage case for storing one or more ophthalmic lenses, the base comprising:
a receptacle for receiving an ophthalmic lens storage case, wherein said storage case is removable from said receptacle and said storage container includes a removable cap attached to said storage case by a fastening mechanism, wherein said removable cap seals off an ambient atmosphere from a storage compartment with the case and wherein said storage case further comprises an alignment artifact;
an electronic circuit mounted on said base, wherein said electronic circuit is capable of controlling a predetermined cycle time of radiation exposure;
a source of disinfecting radiation providing disinfecting radiation to an ophthalmic lens storage compartment in the ophthalmic lens storage case, wherein the disinfecting radiation is capable of permeating the ophthalmic lens storage case and disinfecting an ophthalmic lens stored therein, and wherein said source is controlled by the electronic circuit; and wherein said cap includes a radiation window for directing and focusing disinfecting radiation towards an ophthalmic lens stored in the storage case; and additionally comprising a vibration generation device for providing mechanical movement to a storage case placed in the storage base.

16. The base of claim 15 wherein the vibration generation device comprises a piezoelectric mechanism.

17. The base of claim 15 wherein the piezoelectric mechanism is operated based upon a logical signal generated by a processor.

18. The base of claim 14 additionally comprising a universal serial bus connector for providing logical communication between one, or both of: the processor and the digital storage; and personal processing device.

19. The base of claim 14 additionally comprising a universal serial bus connector for providing an electrical current for operating the storage base.

20. The base of claim 1 additionally comprising an electrical storage for storing power to operate the storage base.

21. The base of claim 20 wherein the electrical storage comprises one or more rechargeable batteries.

22. The base of claim 21 wherein the electrical storage comprises one or more lithium ion batteries.

23. The base of claim 10 wherein a pattern of radiation is based upon a signal from the processor.

* * * * *